| United States Patent [19] | [11] Patent Number: 4,952,410 |
| Armah et al. | [45] Date of Patent: Aug. 28, 1990 |

[54] PHARMACEUTICAL PRODUCTS OF MOXONIDINE AND HYDROCHLOROTHIAZIDE

[75] Inventors: Ben Armah, Hamburg; Wolfgang Stenzel, Reinbek; Vera Plänitz, Henstedt-Ulzburg, all of Fed. Rep. of Germany

[73] Assignee: Beiersdorf AG, Hamburg, Fed. Rep. of Germany

[21] Appl. No.: 272,667

[22] Filed: Nov. 17, 1988

[30] Foreign Application Priority Data

Nov. 24, 1987 [DE] Fed. Rep. of Germany ....... 3739779

[51] Int. Cl.$^5$ ............................................... A61K 9/20
[52] U.S. Cl. .................................... 424/465; 424/400; 424/436; 424/456; 424/464; 424/479; 424/489; 514/869
[58] Field of Search ............... 424/464, 474, 465, 400, 424/436, 456, 479, 489; 514/869

[56] References Cited

U.S. PATENT DOCUMENTS

| 3,113,075 | 12/1963 | Bicking et al. | 516/869 X |
| 4,075,208 | 2/1978 | Wilhelm et al. | 546/210 X |
| 4,255,433 | 3/1981 | Herrmann et al. | 514/326 |
| 4,681,765 | 7/1987 | Guley | 424/455 X |
| 4,793,999 | 12/1988 | Sheth | 424/464 X |

*Primary Examiner*—Thurman K. Page
*Attorney, Agent, or Firm*—Sprung Horn Kramer & Woods

[57] ABSTRACT

Pharmaceutical composition containing moxonidine (4-chloro-6-methoxy-2-methyl-5-(2-imidazolin-2-yl)aminopyrimidine) or its pharmaceutically acceptable salts and hydrochlorothiazide (6-chloro-3,4-dihydro-2H-1,2,4-benzothiadiazine-7-sulphonamide-1,1-dioxide) and, if appropriate, triamterene (2,4,7-triamino-6-phenylpteridine).

13 Claims, No Drawings

PHARMACEUTICAL PRODUCTS OF MOXONIDINE AND HYDROCHLOROTHIAZIDE

The invention relates to new pharmaceutical compositions or products, to the use thereof and to the preparation thereof.

The compound 4-chloro-6-methoxy-2-methyl-5-(2-imidazolin-2-yl)aminopyrimidine (moxonidine) is disclosed as a centrally acting antihypertensive in U.S. Pat. No. 4,323,570.

The compound 6-chloro-3,4-dihydro-2H-1,2,4-benzo-thiadiazine-7-sulphonamide 1,1-dioxide is known as hydrochlorothiazide and was introduced as a diuretic (Merck Index, 10th edition, page 692).

Furthermore, the compound 2,4,7-triamino-6-phenylpteridine is known as triamterene and is an accepted diuretic, compare U.S. Pat. No. 3,081,230.

Hydrochlorothiazide and triamterene have been used for many years in human medicine because of their diuretic properties.

Although moxonidine has proved to be substantially free of undesired side effects, it appears worthwhile to reduce the dose to diminish these side effects, if the strength of action is retained.

It has now been found, surprisingly, that a new pharmaceutical composition which contains moxonidine or its pharmacologically acceptable salts and hydrochlorothiazide has exceptionally beneficial pharmacological properties.

Pharmacologically acceptable acid addition salts are to be understood to be, for example, the salts of d-tartaric acid, maleic acid, fumaric acid, succinic acid, lactic acid, citric acid, cinnamic acid, salicylic acid, adipic acid, acetic acid, propionic acid, p-aminobenzoic acid, methanesulphonic acid, sulphuric acid or phosphoric acid, especially the hydrochloride. Moxonidine is preferably employed as a salt, especially as the hydrochloride.

It has additionally been found that a new pharmaceutical composition which contains moxonidine or its pharmacologically acceptable salts, hydrochlorothiazide and triamterene has unexpected outstanding properties.

The compositions or combinations according to the invention have a synergistic therapeutic action going beyond the action of the individual components. They are used in particular for the treatment of hypertension. The combinations, according to the invention, of the active substances are preferably part of a dosage unit such as, for example, capsule, tablet, film-coated tablet, sugar-coated tablet, suppository, pill or ampoule, but especially of a tablet or film-coated tablet, preferably in the stated ratios by weight.

A particularly preferred pharmaceutical composition contains 1 part by weight of moxonidine and 30 to 400, preferably 40-125, in particular 62.5 or 125, parts by weight of hydrochlorothiazide.

Moxonidine is a centrally acting antihypertensive with a median effective oral dose of 3-10 mg/kg. This lowering effect on blood pressure was found by a plethysmographic method after oral administration to rats.

Hydrochlorothiazide is a proved saluretic with weak and not always adequate antihypertensive properties. Doses of 1-100 mg/kg have no lowering action on blood pressure.

It has now been found, surprisingly, that additional administration of hydrochlorothiazide considerably enhances the lowering action of moxonidine on blood pressure. As is evident from the report of experiments which follows, a moxonidine dose of 3-10 mg/kg is reduced to 0.3-1 mg/kg when hydrochlorothiazide is administered concurrently. The value of this combination is that it is more effective than the individual components.

Hence use of the composition according to the invention permits effective antihypertensive treatment over a longer period.

The pharmaceutical compositions according to the invention preferably contain 1 part by weight of moxonidine and 62.5 to 125 parts by weight of hydrochlorothiazide. For example, a dosage unit according to the invention, such as a tablet or a sugar-coated tablet, contains 0.2 mg of moxonidine, 12.5 mg to 25 mg, in particular 12.5 mg or 25 mg, of hydrochlorothiazide and customary inactive ingredients.

Furthermore, a dosage unit such as a tablet or a sugar-coated tablet containing 0.1 mg of moxonidine, 6.25 mg to 12.5 mg, in particular 6.25 or 12.5 mg, of hydrochlorothiazide and customary inactive ingredients is preferred.

On administration to adults, the daily dose of the active substances administered orally can be, for example, 0.1-0.6 mg of moxonidine and corresponding amounts of hydrochlorothiazide, for example 12.5 to 100 mg of hydrochlorothiazide, preferably about 0.2 mg of moxonidine and 12.5 mg of hydrochlorothiazide up to about 0.4 mg of moxonidine and 25 mg of hydrochlorothiazide. The abovementioned amounts and ratios by weight are also preferred for the individual dosage unit.

The abovementioned doses are particularly preferred for the treatment of hypertension.

The invention also relates to a pharmaceutical composition which contains moxonidine, hydrochlorothiazide and, additionally, triamterene.

A preferred combination containing three active substances is one which contains 1 part by weight of moxonidine, 30 to 400 parts by weight of hydrochlorothiazide and 50 to 800 parts by weight of triamterene.

In addition, in this combination of three active substances too, the abovementioned amounts and ratios by weight of moxonidine and hydrochlorothiazide are preferred.

A particularly preferred combination containing three active substances is one which contains 1 part by weight of moxonidine, 45 to 200 parts by weight of hydrochlorothiazide and 90 to 400 parts by weight of triamterene, but especially 62.5 to 125 parts by weight of hydrochlorothiazide and 125 to 250 parts by weight of triamterene.

It has been found that excretion of potassium can be reduced when the saluretic triamterene, which has been used for years in human medicine, is added to the combination of moxonidine and hydrochlorothiazide.

The use of this composition, according to the invention, containing three active substances is thus especially suitable, as also is the combination containing two active substances, for effective long-term antihypertensive treatment.

These pharmaceutical compositions according to the invention preferably contain 1 part by weight of moxonidine, 62.5 or 125 parts by weight of hydrochlorothiazide and 125 or 250 parts by weight of triamterene. For example, a dosage unit according to the invention, such as a tablet or a sugar-coated tablet, contains 0.2 mg of moxonidine, 12.5 mg to 25 mg, in particular 12.5 mg or 25 mg, of hydrochlorothiazide and 25 mg to 50 mg of triamterene, in particular 25 mg or 50 mg of triamterene, as well as customary inactive ingredients.

Additionally preferred is a dosage unit such as a tablet or a sugar-coated tablet containing 0.1 mg of moxonidine, 6.25 mg to 12.5 mg, in particular 6.25 mg or 12.5 mg, of hydrochlorothiazide and 12.5 mg to 25 mg, in particular 12.5 mg or 25 mg, of triamterene, as well as customary inactive ingredients.

In adults, the daily dose of the active substances administered orally can be, for example, 0.1–0.6 mg of moxonidine and corresponding amounts of hydrochlorothiazide and triamterene, for example about 12.5 mg to 100 mg of hydrochlorothiazide and about 25 mg to 200 mg of triamterene, preferably about 0.2 mg of moxonidine, 12.5 mg of hydrochlorothiazide and 25 mg of triamterene to about 0.4 mg of moxonidine, 25 mg of hydrochlorothiazide and 50 mg of triamterene. The abovementioned ratios by weight and amounts are also preferred for the individual dosage unit.

The stated doses of the two combinations are preferred for the treatment of the said diseases and are particularly preferred for hypertension.

The combinations, according to the invention, of the therapeutic active substances have a pronounced pharmacological action and are valuable medicaments, have, in particular, a diuretic and antihypertensive action, and are particularly suitable in human medicine in the therapy of oedemas of various aetiologies, obesity, especially oedematous obesity, and for the treatment of refractory oedemas, cardiac insufficiency, left ventricular hypertrophy, coronary heart disease, especially angina pectoris and arrhythmias, especially catecholamine-induced arrhythmias, as well as in the long-term treatment of arterial hypertension.

The invention also embraces methods of treatment as well as processes for the preparation of agents for the treatment of the abovementioned diseases.

The pharmaceutical compositions according to the invention can be administered parenterally or via the digestive tract, with oral administration being preferred.

The present invention likewise relates to pharmaceutical compositions or products which contain the active substance combinations according to the invention or pharmaceutically utilizable salts of the active substances.

The active substance combinations or compositions according to the invention can be used without other additives, for example as powders or dispensed into capsules. However, they preferably contain at least one pharmaceutical inactive ingredient, preferably at least one inactive ingredient suitable for oral administration.

These pharmaceutical compositions or products can be, for example, solid or liquid and in the pharmaceutical forms customarily used in human medicine, for example as tablets, sugar-coated tablets, soft gelatin capsules, granules, drinkable suspension, suppositories, pill, syrup, elixir, drops, emulsion, film-coated tablet, dusting powder, oral powder, solution and injectable solution, which can be prepared by the customary processes. It is possible to add to the active substances the inactive ingredients or excipients customarily used for these pharmaceutical compositions, such as carrier materials and binders, for example talc, colloidal silica, gum arabic, lactose, starch, magnesium stearate, cocoa butter, aqueous or non-aqueous vehicles, fats of animal or plant origin, paraffin derivatives, glycols, various wetting agents, dispersants or emulsifiers and/or preservatives.

The active substances can be mixed with the inactive ingredients or excipients such as carrier materials and binders in the customary manner and granulated wet or dry. It is possible, depending on the nature of the additives used, where appropriate also to obtain, by simple mixing, a powder which can be tabletted directly. The granules or powder can be directly dispensed into capsules or, preferably, compressed to tablet cores in a customary manner.

The invention also relates to the processes for the preparation of the combinations and of the agents, products and compositions which contain these combinations.

The processes for the preparation of the pharmaceutical compositions are characterized in that active substances or combinations according to the invention are processed, where appropriate together with a pharmaceutical inactive ingredient, to a pharmaceutical product.

Tablets are preferably prepared in several process steps:

(a) Hydrochlorothiazide and, where appropriate, triamterene are mixed dry with a carrier material, preferably lactose.

(b) Moxonidine or a moxonidine salt is dissolved in a solvent or solvent mixture (for example with equal parts by volume), preferably composed of water, alcohols and halogenated hydrocarbons (for example methylene chloride, chloroform), containing a binder, preferably polyvinyl pyrrolidone (PVP), where appropriate with application of heat.

(c) The powder mixture obtained as in process step (a) is moistened with the solution obtained as in process step (b). The composition is kneaded and then granulated. The granules are dried, preferably at elevated temperature, for example in a fluidized-bed drier or a tray cabinet. The dried granules are then broken up in a screening and milling machine.

(d) Inactive ingredients which are used where appropriate, such as flow regulators, fillers, lubricants, release agents and disintegrants (FDR complex), are preferably mixed with starches.

(e) The broken-up granules obtained as in process step (c) are mixed with the mixture from d) to give a mixture ready for tabletting, and the latter is then compressed to tablets by customary processes.

Percentage data relate to weight.

The examples which follow explain the invention without, however, limiting it.

PHARMACEUTICAL COMPOSITIONS

Example 1

Tablets are prepared corresponding to the following formulation:
Hydrochlorothiazider: 12.5 mg
Moxonidine: 0.2 mg
Excipient (q.s.): 250 mg
(Excipient: polyvinylpyrrolidone, maize starch, treated starch, lactose, magnesium stearate, talc).

Example 2

Tablets are prepared corresponding to the following formulation:
Hydrochlorothiazide: 12.5 mg
Moxonidine: 0.1 mg Excipient (q.s.): 250 mg
(Excipient: polyvinylpyrrolidone, maize starch, treated starch, lactose, magnesium stearate, talc).

Example 3

Tablets are prepared corresponding to the following formulation:
Triamterene: 25 mg
Hydrochlorothiazide: 12.5 mg
Moxonidine: 0.2 mg
Excipient (q.s.): 250 mg
(Excipient: polyvinylpyrrolidone, maize starch, treated starch, lactose, magnesium stearate, talc).

Example 4

Tablets are prepared corresponding to the following formulation:
Triamterene: 25 mg
Hydrochlorothiazide: 12.5 mg
Moxonidine: 0.1 mg
Excipient (q.s.): 250 mg
(Excipient: polyvinylpyrrolidone, maize starch, treated starch, lactose, magnesium stearate, talc).

Example 5

(a) 6.25 kg of hydrochlorothiazide and 87.25 kg of lactose (or 74.75 kg of lactose and 12.5 kg of triamterene in the case of the combination of three active substances) are mixed dry.
(b) 0.1 kg of moxonidine in the form of the hydrochloride, and 1 kg of PVP are dissolved in a solvent mixture composed of water, ethanol and methylene chloride with application of heat.
(c) The powder mixture obtained as in process step (a) is moistened with the solution obtained as in process step (b). The composition is kneaded and then granulated. The granules are dried in a fluidized-bed drier at about 50° C. for one hour. The dried granules are then broken up in a screening and milling machine.
(d) 0.4 kg of a mixture of customary flow regulator, disintegrant and release agent (FDR complex) is mixed with 5 kg of starch.
(e) The broken-up granules obtained as in process step (c) are mixed with the mixture from (d) to give a mixture ready for tabletting, and the latter is then compressed to tablets weighing 200 mg by customary processes.

Tablets weighing 100 mg and 300 mg are obtained analogously.

COMPOSITION OF TABLETS WEIGHING 100 MG, 200 MG AND 300 MG (in Per Cent by Weight)

|  | (a) | (b) |
|---|---|---|
| Lactose | 87.25 | 74.75 |
| PVP | 1 | 1 |
| Starch | 5 | 5 |
| FDR complex | 0.4 | 0.4 |
| Moxonidine | 0.1 | 0.1 |
| Hydrochlorothiazide | 6.25 | 6.25 |
| Triamterene | — | 12.5 |

To treat the said diseases, especially hypertension, the described tablets can be administered once, twice or several times a day.

PHGARMACOLOGICAL INVESTIGATIONS

1. Reduction in Arterial Blood Pressure with Various Doses of Moxonidine

The experiments were carried out by methods known from the literature (Armah, B.; Drug Research, Vol. 27, (II) 1977, page 1882–1884).

TABLE 1

Reduction in arterial blood pressure (in mm Hg) with various doses of moxonidine

| Dose (mg/kg oral) |  | Reduction in systolic pressure (mm Hg) |
|---|---|---|
| Moxonidine | 0.3 | 10 |
| Moxonidine | 1.0 | 20 |
| Moxonidine | 3.0 | 50 |
| Moxonidine | 10.0 | 60 |

The experiments were carried out by methods known from the literature (Armah, B.; Drug Research, Vol. 27, (II) 1977, page 1882–1884).

TABLE 2

Effect of hydrochlorothiazide on the systolic blood pressure of conscious genetically hypertensive rats

| Dose (mg/kg oral) | Reduction in systolic pressure (mm Hg) |
|---|---|
| 1 | ± 0 |
| 3 | ± 0 |
| 10 | ± 0 |
| 30 | 2 ± 4 |
| 60 | 4 ± 6 |

The experiments were carried out by methods known from the literature (Armah, B.; Drug Research, Vol. 27, (II) 1977, page 1882–1884).

TABLE 3

Effect of the moxonidine-hydrochlorothiazide combination on the systolic blood pressure of conscious genetically hypertensive rats

| Addition of hydrochlorothiazide | | Moxonidine doses (pressure in mm Hg) | |
|---|---|---|---|
| mg/kg | 0.3 mg/kg | 1 mg/kg | 3 mg/kg |
| 0 | 10 mm Hg | 20 mm Hg | 50 mm Hg |
| 30 | 30 mm Hg | 40 mm Hg | 50 mm Hg |
| 60 | 40 mm Hg | 50 mm Hg above | 50 mm Hg |

The conclusion from the preceding tables is that additional administration of hydrochlorothiazide considerably enhances the lowering action of moxonidine on blood pressure, so that when the combination is administered it is possible to reduce the moxonidine dosages customary for the treatment of hypertension. This makes it possible to diminish considerably the side effects, which are already slight in any case. This is because it has been shown that a moxonidine dose of 1 mg/kg no longer has a sedative property.

The addition of triamterene (30 mg/kg p.o.) to the moxonidine-hydrochlorothiazide combination (3 +30 mg/kg p.o.) when given by oral route to male spontaneously hypertensive rats, caused a further reduction of systolic blood pressure by at least 15–20%, more than the moxonidine and hydrochlorothiazide combination alone.

We claim:

1. Pharmaceutical composition containing 1 part by weight of moxonidine (4-chloro-6-methoxy-2-methyl-5(2-imidazolin-2-yl)amino-pyrimidein) or its pharmaceutically acceptable salts and 30 to 400 parts by weight of hydrochlorothiazide (6-chloro-3,4-dihydro-2H-1,2,4-benzothiadiazine-7-sulphonamide-1,1-dioxide).

2. Pharmaceutical composition containing 1 part by weight of moxonidine (4-chloro-6-methoxy-2-methyl-5-(2-imidazolin-2yl)amino-pyrimidein) or its pharmaceutically acceptable salts and 30 to 400 parts by weight of hydrochlorothiazide (6-chloro-3,4-dihydro-2H-1,2,4-benzothiadiazine-7-sulphonamide-1,1-dioxide) and triamterene (2,4,7-triamino6-phdnylpteridine).

3. Pharmaceutical composition according to claim 2, characterized in that it contains 50 to 800 parts by weight of triamterene.

4. Pharmaceutical composition according to claim 1, characterized in that it contains 1 part by weight of moxonidine and 62.5 to 125 parts by weight of hydrochlorothiazide.

5. Pharmaceutical composition according to claim 2, characterized in that it contains 1 part by weight of moxonidine, 62.5 to 125 parts by weight of hydrochlorothiazide and 125 to 250 parts by weight of triamterene.

6. Pharmaceutical composition according to claim 1 containing pharmaceutical inactive ingredients suitable for oral administration.

7. Pharmaceutical composition according to claim 2 containing pharmaceutical inactive ingredients suitable for oral administration.

8. Pharmaceutical composition according to claim 1 in the form of tablets or sugar-coated tablets containing 0.2 mg of moxonidine and 12.5 mg of hydrochlorothiazide.

9. Pharmaceutical composition according to claim 2 in the form of tablets or sugar-coated tablets containing 0.2 mg of moxonidine, 12.5 mg of hydrochlorothiazide and 25 mg of triamterene.

10. A method of treating a patient having a diuretic or hypertensive condition which comprises administering to such patient an amount effective therefor of a composition according to claim 1.

11. A method of treating a patient having a diuretic or hypertensive condition which comprises administering to such patient an amount effective therefor of a composition according to claim 2.

12. Process for the preparation of the pharmaceutical compositions according to claim 1, characterized in that
 (a) hydrochlorothiazide is mixed dry with a carrier material.
 (b) moxonidine or a moxonidine salt is dissolved in a solvent or solvent mixture composed of water, alcohols and halogenated hydrocarbons containing a binder,
 (c) moistening the powder mixture obtained in step (a) with the solution obtained in step (b), kneading the composition, granulating, drying, breaking up the dried granules in a screening and milling machine,
 (d) optionally mixing flow regulators, fillers, lubricants, release agents or disintegrants with starches, and
 (e) mixing the broken-up granules obtained in step (c) with the mixture from (d), and then compressing the mixture to tablets.

13. Process for the preparation of the pharmaceutical compositions according to claim 2, characterized in that
 (a) hydrochlorothiazide and triamterene are mixed dry with a carrier material,
 (b) moxonidine or a moxonidine salt is dissolved in a solvent or solvent mixture composed of water, alcohols and halogenated hydrocarbons containing a binder,
 (c) moistening the powder mixture obtained in step (a) with the solution obtained instep (b), kneading the composition, granulating, drying, breaking up the dried granulares in a screening and milling machine,
 (d) optionally mixing flow regulators, fillers, lubricants, release agents or disintegrants with starches, and
 (e) mixing the broken-up granulares obtained in step (c) with the mixture from (d), and then compressing the mixture to tablets.

* * * * *